US012251407B2

United States Patent
Dai et al.

(10) Patent No.: US 12,251,407 B2
(45) Date of Patent: Mar. 18, 2025

(54) **USE OF *MEGAMONAS FUNIFORMIS* IN PREVENTING AND/OR TREATING METABOLIC DISEASES**

(71) Applicant: BGI SHENZHEN, Guangdong (CN)

(72) Inventors: Ying Dai, Guangdong (CN); Yuanqiang Zou, Guangdong (CN); Liang Xiao, Guangdong (CN)

(73) Assignee: BGI SHENZHEN, Guangdong (CN)

( * ) Notice: Subject to any disclaimer, the term of this patent is extended or adjusted under 35 U.S.C. 154(b) by 910 days.

(21) Appl. No.: 17/296,423

(22) PCT Filed: Dec. 7, 2018

(86) PCT No.: PCT/CN2018/119909
§ 371 (c)(1),
(2) Date: May 24, 2021

(87) PCT Pub. No.: WO2020/113579
PCT Pub. Date: Jun. 11, 2020

(65) Prior Publication Data
US 2022/0031770 A1   Feb. 3, 2022

(51) Int. Cl.
*A61P 9/10* (2006.01)
*A61K 35/741* (2015.01)
*A61P 3/00* (2006.01)

(52) U.S. Cl.
CPC .............. *A61K 35/741* (2013.01); *A61P 3/00* (2018.01)

(58) Field of Classification Search
CPC . A61K 35/741; A61P 3/00; A61P 1/00; A61P 3/04; A61P 3/06; A61P 3/10; A61P 9/10; C12R 2001/01; C12N 1/20; C12N 1/205; Y02A 50/30
See application file for complete search history.

(56) References Cited

FOREIGN PATENT DOCUMENTS

| CN | 104546938 A | 4/2015 |
|---|---|---|
| CN | 107847531 A | 3/2018 |
| WO | 2018187272 A1 | 10/2018 |
| WO | 2019051790 A1 | 3/2019 |

OTHER PUBLICATIONS

Patent office sequence search GenBank Accession No. EF400799 (Year: 2024).*
Zou, Yuanqiang "Taxonomy of healthy gut microbial strain TF01-11~T" A Dissertation Submitted for the Degree of Master. Submitted 2016. (2017) South China University of Technology. English Machine Translation.
Zhang, X. Y. et al. "Human Gut Microbiota Changes Reveal the Progression of Glucose Intolerance" PLoS One. (2013) vol. 8, No. 8, e71108, pp. 1-11.
He, F. P. et al. "Metagenomic Analysis of Captive Amur Tiger Faecal Microbiome" BMC Veterinary Research, (2018) vol. 14, No. 379, pp. 1-8.
Li, M. et al. "Accession No. EF400799.1" Genbank., (2008) Features, Origin.
International Search Report issued for PCT/CN2018/119909, dated Sep. 10, 2019.
Written Opinion of the International Searching Authority issued for PCT/CN2018/119909, dated Sep. 10, 2019.

* cited by examiner

*Primary Examiner* — Adam Weidner
*Assistant Examiner* — Tiffany M Gough
(74) *Attorney, Agent, or Firm* — Westman, Champlin & Koehler, P.A.; Z. Peter Sawicki; Amanda M. Prose

(57) ABSTRACT

Provided is a use of *Megamonas funiformis* in the prevention and/or treatment of metabolic diseases. *Megamonas funiformis* has the function of preventing and/or treating metabolic diseases (such as obesity, diabetes, atherosclerosis-related diseases, cardiovascular disease and hyperuricemia).

19 Claims, No Drawings
Specification includes a Sequence Listing.

SEQUENCE LISTING

<160> NUMBER OF SEQ ID NOS: 3

<210> SEQ ID NO 1
<211> LENGTH: 1423
<212> TYPE: DNA
<213> ORGANISM: Megamonas funiformis

<400> SEQUENCE: 1

```
ttaacacatg caagtcgaac ggggtgttta tttcggtaaa caccaagtgg cgaacgggtg      60
agtaacgcgt aagcaatcta ccttcaagat ggggacaaca cttcgaaagg ggtgctaata     120
ccgaatgaat gtaagagtat cgcatgagac acttactaaa ggaggcctct gaaaatgctt     180
ccgcttgaag atgagcttgc gtctgattag ctagttggtg agggtaaagg cccaccaagg     240
cgacgatcag tagccggtct gagaggatga acggccacat tgggactgag acacggccca     300
gactcctacg ggaggcagca gtggggaatc ttccgcaatg ggcgaaagcc tgacggagca     360
acgccgcgtg aacgatgaag gtcttaggat cgtaaagttc tgttgttagg gacgaagggt     420
aagaataata atacggtttt tatttgacgg tacctaacga ggaagccacg gctaactacg     480
tgccagcagc cgcggtaata cgtaggcggc aagcgttgtc cggaattatt gggcgtaaag     540
ggagcgcagg cgggaaacta agcggatctt aaaagtgcgg ggctcaaccc cgtgatgggg     600
tccgaactgg ttttcttgag tgcaggagag gaaagcggaa ttcccagtgt agcggtgaaa     660
tgcgtagata ttgggaagaa caccagtggc gaaggcggct ttctggactg taactgacgc     720
tgaggctcga aagctagggt agcgaacggg attagatacc ccggtagtcc tagccgtaaa     780
cgatggatac taggtgtggg aggtatcgac cccttccgtg ccggagttaa cgcaataagt     840
atcccgcctg gggagtacgg ccgcaaggtt gaaactcaaa ggaattgacg ggggcccgca     900
caagcggtgg agtatgtggt ttaattcgac gcaacgcgaa gaaccttacc aagacttgac     960
attgattgaa aggcctagag ataggtccct tctcttcgga gaacaagaaa acaggtggtg    1020
catggctgtc gtcagctcgt gtcgtgagat gttgggttaa gtcccgcaac gagcgcaacc    1080
cctatactat gttgccagca ttacggatgg gaactcatag tagactgccg cggacaacgc    1140
ggaggaaggc ggggatgacg tcaagtcatc atgccccctta cgtcttgggc tacacacgta    1200
ctacaatggg atgaacagag ggaagcgaaa tcgcgaggtg gagcggatcc ctaaaagcat    1260
```

```
ctctcagttc ggattgtagg ctgaaactcg cctacatgaa gtcggaatcg ctagtaatcg    1320
caggtcagca tactgcggtg aatacgttcc cgggccttgt acacaccgcc cgtcacacca    1380
cgaaagtcat tcacacccga agccggctaa gggcctatgg tac                     1423

<210> SEQ ID NO 2
<211> LENGTH: 20
<212> TYPE: DNA
<213> ORGANISM: Artificial sequence
<220> FEATURE:
<223> OTHER INFORMATION: synthetic sequence

<400> SEQUENCE: 2
agagtttgat catggctcag                                                 20

<210> SEQ ID NO 3
<211> LENGTH: 22
<212> TYPE: DNA
<213> ORGANISM: Artificial sequence
<220> FEATURE:
<223> OTHER INFORMATION: synthetic sequence

<400> SEQUENCE: 3
tagggttacc ttgttacgac tt                                              22
```

USE OF *MEGAMONAS FUNIFORMIS* IN PREVENTING AND/OR TREATING METABOLIC DISEASES

CROSS-REFERENCE TO RELATED APPLICATIONS

This application is a US National Phase application based upon PCT Application No. PCT/CN2018/119909 filed with the National Intellectual Property Administration of PRC on Dec. 7, 2018, the entire content of which is incorporated herein by reference.

FIELD

The present disclosure relates to the field of microorganism, in particular to the use of *Megamonas funiformis* in the prevention and/or treatment of metabolic diseases.

BACKGROUND

Obesity, diabetes, atherosclerosis (AS), cardiovascular disease and hyperuricemia all belong to metabolic diseases. Metabolic diseases include lipid metabolism disease, purine metabolism disease and insulin metabolism disease, in which the lipid metabolism disease includes obesity, atherosclerosis related diseases, cardiovascular disease and the like, the purine metabolism disease includes hyperuricemia and the like, and the insulin metabolism disease includes diabetes and the like.

Obesity is a chronic disease, which can be caused by several factors and is of a yet unclear origin of disease. Meanwhile, obesity is also an inducer of a series of diseases, such as hypertension, diabetes, coronary heart disease, gallbladder disease, osteoarthritis, sleep apnea, breathing disorder, hysteroma, prostate cancer, breast cancer and colon cancer. According to the report of National Institutes of Health (NIH), currently there are about 97 million Americans being overweight and obese, among them up to about 15.1 million people suffer from obesity-related Type II diabetes, and about 0.2 million people die from obesity-related diseases every year. Further, it is indicated by current studies that the diversity of gut microbes in obese people is remarkably lower than that in normal people.

Diabetes is a disease manifested as abnormally high blood glucose caused by a variety of factors (generally including genetic factors, environmental factors and unhealthy lifestyle), which belongs to a metabolic disorder mainly due to insufficient insulin secretion or insulin dysfunction. The type II diabetes (T2D) is a type of non-insulin dependent diabetes, accounting for 90% of all diabetes patients. A large number of studies have shown that the onset of type II diabetes mainly resulted from insulin resistance and low-level inflammation reaction is closely related to the disorder of intestinal flora which is tightly associated to the regulation of energy balance and inflammatory response in a host.

Atherosclerosis (AS) is the main cause of coronary heart disease, cerebral infarction and peripheral vascular disease, in which lipid metabolism abnormity is the basis of atherosclerotic lesions. The atherosclerosis is characterized by arteries involved lesions, which are initiated from intima, generally occurring the accumulation of lipids and complex sugars, bleeding and thrombosis, followed by fibrous tissue hyperplasia and calcium deposition, and then gradual metamorphosis and calcification of middle layer of artery which results in thickening and hardening of arterial wall and narrowing of vascular cavity. Once the lesions, always involving in the large and medium-sized muscular arteries, develop enough to block the arterial cavity, the tissues or organs supplied by the arteries will be ischemic or necrotic. The atherosclerosis which is named after the yellow atheromatous appearance of lipid accumulated in the intima of arteries, is caused by combined factors, with complicated pathogenesis. Among them, the main risk factors for atherosclerosis include hypertension, hyperlipidemia and heavy smoking, as well as diabetes, obesity, genetic factors and the like.

Coronary heart disease is a heart disease caused by myocardial ischemia and hypoxia by coronary atherosclerosis, also known as ischemic heart disease. The pathological pathogenesis of coronary heart disease is mainly the increased blood lipids due to lipid metabolism disorder, lipid deposition and infiltration in the inner wall of blood vessel, formation of vascular endothelial foam cells, and chronic inflammatory reactions in blood vessel wall that damage the function and morphology of coronary vascular endothelial cells, formation of vascular endothelial atherosclerotic plaque, further plaque rupture, thrombosis, vascular stenosis or occlusion resulting in coronary blood circulation disorder, myocardial ischemia, damaged myocardial cells, and cardiac insufficiency caused. With the improvement of living standards, the incidence and mortality of coronary heart disease in our country have increased yearly and exhibit a trend of getting younger.

Gout is a group of diseases caused by purine metabolism disorder and/or decreased uric acid excretion. Pathological studies indicate that the onset of gout is mainly related to purine metabolism disorder through hereditary or acquired causes. Clinicopathological manifestations of gout include hyperuricemia and the resulting recurrent gouty acute arthritis, gout stone deposition, gout stone chronic arthritis and joint deformities, often involving kidney thus causing formation of chronic interstitial nephritis and uric acid nephrolithiasis, also can leading to acute renal failure by uric acid stone. The latest studies have found that this disease shows a trend of getting younger. There is no medical cure method for hyperuricemia currently.

The existing means for treating obesity include dieting, exercise, behavior therapy, drug therapy and rehabilitation surgery. The hypoglycemic drugs for diabetes include sulfonylureas, α-glucosidase inhibitors and biguanides. Coronary heart disease is treated mainly through drugs, intervention or surgery. Hyperuricemia is treated by drugs including colchicine, aspirin, indomethacin and the like, or via intervention or surgery.

For the treatment means of obesity, dieting and exercise may do not bring significant effect to the general public for the requirement of long-term persistence, thereby most people give up; the removal of body fat may achieve an immediate result, but having limiting factors such as the risk of surgery, effect of body fat removal, high cost and the like; and treatment via drugs such as phenylpropanolamine (PPA), orlistat (Xenical III) and sibutramine (Reductil™) may cause local or systemic allergies to drugs. Drugs for treating diabetes may cause a variety of side effects, such as severe damage of liver and kidney, easy to incur bloating, diarrhea and the like, and is prone to inactivation in a long-term use. For the treatment means of coronary heart disease, drug treatment may cause side effects of headaches, nausea and vomiting, skin allergies and the like; interventional therapy, despite having a great progress, has the problems of a high probability of recurrence, and restenosis which has been limiting the development of stents, in which the existing drug stents though capable of preventing recurrence, may lead to the formation of thrombosis, even incur sudden death in severe cases; and surgical treatment is also faced with disadvantages of large surgical trauma, a high cost, a high risk for elderly and weak patients as well as patients with severely impaired function of vital organs. Indomethacin as a common oral agent for the treatment of hyperuricemia has the side effects including gastrointestinal reactions, dizziness, rash and water and sodium retention, which is contraindicated for patients with peptic ulcer. Intervention and surgery have problems such as postoperative restenosis, a high cost and the like, and cannot cure acute onset of arthritis, urate nephropathy and uric acid urinary stone from the source.

Therefore, there is an urgent need in the art to develop a new and non-toxic and side effect composition for the prevention and/or treatment of metabolic diseases, especially a pharmaceutical composition.

SUMMARY

The present disclosure in embodiments provides a new and non-toxic and side effect composition for the prevention and/or treatment of metabolic diseases.

In a first aspect, provided in embodiments is use of *Megamonas funiformis* in the preparation of a composition for preventing and/or treating metabolic diseases.

In a preferred embodiment, the *Megamonas funiformis* has a sequence of 16 s rDNA as shown in SEQ ID NO: 1 or with 99% or above sequence similarity to SEQ ID NO: 1.

In a preferred embodiment, the *Megamonas funiformis* is *Megamonas funiformis* AF24-28AC with a deposit number of GDMCC 60093, *Megamonas funiformis* DSM 19343 or *Megamonas funiformis* JCM 14723, or a combination thereof.

In a preferred embodiment, the *Megamonas funiformis* is derived from intestine, animal faeces, a fermentation tank and/or an anaerobic reactor.

In a preferred embodiment, the *Megamonas funiformis* is derived from human or non-human mammals.

In a preferred embodiment, the non-human mammal includes rodents such as mice and rats, and primates such as monkey.

In a preferred embodiment, the metabolic disease comprises a lipid metabolism disease, a purine metabolism disease and/or an insulin metabolism disease.

In a preferred embodiment, the metabolic disease is selected from the group consisting of obesity, diabetes, atherosclerosis-related diseases, cardiovascular disease, hyperuricemia or a combination thereof.

In a preferred embodiment, the atherosclerosis-related diseases are selected from the group consisting of coronary heart disease, coronary artery disease (CAD), atherosclerotic heart disease, atherosclerotic cardiovascular disease, ischemic heart disease or a combination thereof.

In a preferred embodiment, the cardiovascular disease is selected from the group consisting of acute coronary syndrome, angina pectoris, arterial sclerosis, atherosclerosis, carotid atherosclerosis, cerebrovascular disease, cerebral infarction, congestive heart failure, congenital heart disease, coronary heart disease, coronary artery disease, coronary plaque stabilization, dyslipidemia, dyslipoproteinemia, endothelial dysfunction, familial hypercholesterolemia, familial combined hyperlipidemia, hypo-α lipoproteinemia, hypertriglyceridemia, hyper-β lipoproteinemia, hypercholesterolemia, hypertension, hyperlipidemia, intermittent claudication, ischemia, ischemia reperfusion injury, ischemia heart disease, myocardial ischemia, metabolic syndrome, multiple cerebral infarction dementia, myocardial infarction, obesity, peripheral vascular disease, reperfusion injury, restenosis, renal atherosclerosis, rheumatic heart disease, stroke, thrombosis disorder, transient ischemic attacks, and lipoprotein abnormalities related to Alzheimer's disease, obesity, diabetes, general X, impotence, multiple sclerosis, Parkinson's disease, inflammatory disease, or combinations thereof.

In a preferred embodiment, the composition comprises: (a) a safe and effective amount of *Megamonas funiformis* and/or its metabolites, and (b) a food acceptable or pharmaceutically acceptable carrier.

In a preferred embodiment, the composition further comprises a growth factor, preferably a milk growth factor.

In a preferred embodiment, the composition is selected from the group consisting of a food composition, a health care composition, a pharmaceutical composition, a beverage composition, a feed composition or a combination thereof.

In a preferred embodiment, the composition is an oral preparation.

In a preferred embodiment, the composition is a liquid preparation, a solid preparation or a semi-solid preparation.

In a preferred embodiment, the dosage form of the composition is selected from the group consisting of powder, pulvis, tablet, sugar coating agent, capsule, granule, suspension, solution, syrup, drop, sublingual tablet or a combination thereof.

In a preferred embodiment, the food composition includes an emulsion product, a solution product, a powder product or a suspension product.

In a preferred embodiment, the food composition includes dairy, milk powder or emulsion.

In a preferred embodiment, the liquid preparation is selected from the group consisting of a solution product or a suspension product.

In a preferred embodiment, the composition comprises $1 \times 10^{-1}$ to $1 \times 10^{20}$ cfu/mL or cfu/g of *Megamonas funiformis*, preferably $1 \times 10^{4}$ to $1 \times 10^{15}$ cfu/mL or cfu/g of *Megamonas funiformis*.

In a preferred embodiment, the composition comprises 0.0001 to 99 wt %, preferably 0.1 to 90 wt % of *Megamonas funiformis* and/or its metabolites, based on the total weight of the composition.

In a preferred embodiment, the composition is in a unit dosage form, i.e., one tablet, one capsule or one vial, and the composition in each unit dosage form is of a mass of 0.05 g to 5 g, preferably 0.1 g to 1 g.

In a preferred embodiment, the composition further comprises probiotics and/or prebiotics.

In a preferred embodiment, the composition is a probiotic agent, a microecological preparation or a pharmaceutical preparation.

In a preferred embodiment, the probiotic agent is a probiotic milk product or a probiotic tablet.

In a preferred embodiment, the probiotics are selected from the group consisting of Lactic acid bacteria, *Bifidobacteria, Lactobacillus acidophilus* or a combination thereof.

In a preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In a preferred embodiment, the composition further contains a substance capable of maintaining the viability of *Megamonas funiformis*, such as a protective agent.

In a preferred embodiment, the substance capable of maintaining the viability of *Megamonas funiformis* such as a protective agent is selected from the group consisting of cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof, especially Vitamin C.

In a preferred embodiment, the substance capable of maintaining the viability of *Megamonas funiformis* such as a protective agent is of a weight ratio of 0.1% to 2%, preferably 0.5% to 1.5%, more preferably 0.5% to 1.0%, based on the total weight of the composition.

In a preferred embodiment, the substance capable of maintaining the viability of *Megamonas funiformis* such as a protective agent is of an amount of 1 mg to 20 mg, preferably 5 mg to 15 mg, more preferably 5 mg to 10 mg, based on 1 g of the composition.

In a second aspect, provided in embodiments is use of *Megamonas funiformis* in the preparation of a composition for exhibiting one or more activities from the group consisting of:
(i) reducing a blood glucose level in mammals;
(ii) ameliorating glucose intolerance in mammals;
(iii) ameliorating myocardial ischemia in mammals;
(iv) reducing a blood uric acid level in mammals;
(v) reducing a blood lipid level in mammals;
(vi) reducing body weight of mammals; and
(vii) ameliorating vasculopathy in mammals.

In a preferred embodiment, the mammals include human or non-human mammals.

In a preferred embodiment, the non-human mammal includes rodents such as mice and rats, and primates such as monkey.

In a preferred embodiment, ameliorating vasculopathy in mammals includes amelioration of one or more indicators selected from the group consisting of blood viscosity, blood rheology, blood pressure, blood lipids (such as triglyceride, total cholesterol, high-density lipoprotein, low-density lipoprotein) and ST segment of electrocardiogram.

In a preferred embodiment, reducing a blood lipid level in mammals includes reducing total cholesterol level, triglyceride level, low-density lipoprotein level and/or blood viscosity level in blood.

In a preferred embodiment, reducing body weight of mammals indicates that the body weight of mammal in an experimental group is reduced by 10% or above, preferably 15% to 20% compared to that of mammal in a model group.

In a preferred embodiment, ameliorating myocardial ischemia in mammals includes reducing ST segment displacement of myocardial ischemia in the mammal.

In a third aspect, provided in embodiments is *Megamonas funiformis* or a composition comprising *Megamonas funiformis* for use in the prevention and/or treatment of metabolic diseases.

In a preferred embodiment, the *Megamonas funiformis* has a sequence of 16 s rDNA as shown in SEQ ID NO: 1 or with 99% or above sequence similarity to SEQ ID NO: 1.

In a preferred embodiment, the *Megamonas funiformis* is *Megamonas funiformis* AF24-28AC with a deposit number of GDMCC 60093, *Megamonas funiformis* DSM 19343 or *Megamonas funiformis* JCM 14723, or a combination thereof.

In a preferred embodiment, the *Megamonas funiformis* is derived from intestine, animal faeces, a fermentation tank and/or an anaerobic reactor.

In a preferred embodiment, the *Megamonas funiformis* is derived from human or non-human mammals.

In a preferred embodiment, the non-human mammal includes rodents such as mice and rats, and primates such as monkey.

In a preferred embodiment, the metabolic disease comprises a lipid metabolism disease, a purine metabolism disease and/or an insulin metabolism disease.

In a preferred embodiment, the metabolic disease is selected from the group consisting of obesity, diabetes, atherosclerosis-related diseases, cardiovascular disease, hyperuricemia or a combination thereof.

In a preferred embodiment, the composition comprises: (a) a safe and effective amount of *Megamonas funiformis* and/or its metabolites, and (b) a food acceptable or pharmaceutically acceptable carrier.

In a preferred embodiment, the composition further comprises a growth factor, preferably a milk growth factor.

In a preferred embodiment, the composition is selected from the group consisting of a food composition, a health care composition, a pharmaceutical composition, a beverage composition, a feed composition or a combination thereof.

In a preferred embodiment, the composition is an oral preparation.

In a preferred embodiment, the composition is a liquid preparation, a solid preparation or a semi-solid preparation.

In a preferred embodiment, the dosage form of the composition is selected from the group consisting of powder, pulvis, tablet, sugar coating agent, capsule, granule, suspension, solution, syrup, drop, sublingual tablet or a combination thereof.

In a preferred embodiment, the food composition includes an emulsion product, a solution product, a powder product or a suspension product.

In a preferred embodiment, the food composition includes dairy, milk powder or emulsion.

In a preferred embodiment, the liquid preparation is selected from the group consisting of a solution product or a suspension product.

In a preferred embodiment, the composition comprises $1\times10^{-1}$ to $1\times10^{20}$ cfu/mL or cfu/g of *Megamonas funiformis*, preferably $1\times10^{4}$ to $1\times10^{15}$ cfu/mL or cfu/g of *Megamonas funiformis*.

In a preferred embodiment, the composition comprises 0.0001 to 99 wt %, preferably 0.1 to 90 wt % of *Megamonas funiformis* and/or its metabolites, based on the total weight of the composition.

In a preferred embodiment, the composition is in a unit dosage form, i.e., one tablet, one capsule or one vial, and the composition in each unit dosage form is of a mass of 0.05 g to 5 g, preferably 0.1 g to 1 g.

In a preferred embodiment, the composition further comprises probiotics and/or prebiotics.

In a preferred embodiment, the composition is a probiotic agent, a microecological preparation or a pharmaceutical preparation.

In a preferred embodiment, the probiotic agent is a probiotic milk product or a probiotic tablet.

In a preferred embodiment, the probiotics are selected from the group consisting of Lactic acid bacteria, *Bifidobacteria*, *Lactobacillus acidophilus* or a combination thereof.

In a preferred embodiment, the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

In a preferred embodiment, the *Megamonas funiformis* and/or its metabolites are combined with prebiotics, optionally also combined with probiotics, which can be made into forms such as a tabletting candy, a capsule or the like, so as to further change the type of probiotic agent, thereby maintaining the activity of *Megamonas funiformis* and achieving the corresponding preventive and/or therapeutic efficacy.

In a preferred embodiment, the composition further contains a substance capable of maintaining the viability of *Megamonas funiformis*, such as a protective agent.

In a preferred embodiment, the substance capable of maintaining the viability of *Megamonas funiformis* such as a protective agent is selected from the group consisting of cysteine, glutathione, butyl hydroxyanisole, dibutylmethyl-toluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof.

In a preferred embodiment, the substance capable of maintaining the viability of *Megamonas funiformis* such as a protective agent is of a weight ratio of 0.1% to 2%, preferably 0.5% to 1.5%, more preferably 0.5% to 1.0%, based on the total weight of the composition.

In a preferred embodiment, the substance capable of maintaining the viability of *Megamonas funiformis* such as a protective agent is of an amount of 1 mg to 20 mg, preferably 5 mg to 15 mg, more preferably 5 mg to 10 mg, based on 1 g of the composition.

In a fourth aspect, provided in embodiments is *Megamonas funiformis* or a composition comprising *Megamonas funiformis* for use in exhibiting one or more activities from the group consisting of:
 (i) reducing a blood glucose level in mammals;
 (ii) ameliorating glucose intolerance in mammals;
 (iii) ameliorating myocardial ischemia in mammals;
 (iv) reducing a blood uric acid level in mammals;
 (v) reducing a blood lipid level in mammals;
 (vi) reducing body weight of mammals; and
 (vii) ameliorating vasculopathy in mammals.

In a fifth aspect, provided in embodiments is a method for preparing the composition of the third aspect or the fourth aspect, comprising:
 mixing (a) a *Megamonas funiformis* and/or its metabolites with (b) a food acceptable or pharmaceutically acceptable carrier to form the composition of the third aspect or the fourth aspect.

In a preferred embodiment, the method further comprises a step of mixing with probiotics and/or prebiotics.

In a preferred embodiment, the method further comprises a step of mixing with a substance capable of maintaining the vitality of *Megamonas funiformis*.

In a sixth aspect, provided in embodiments is a method for preventing and/or treating metabolic diseases, comprising:
 administering a *Megamonas funiformis* or a composition comprising the *Megamonas funiformis* to a subject in need to prevent and/or treat the metabolic diseases.

In a preferred embodiment, the *Megamonas funiformis* has a sequence of 16 s rDNA as shown in SEQ ID NO: 1 or with 99% or above sequence similarity to SEQ ID NO: 1.

In a preferred embodiment, the *Megamonas funiformis* is *Megamonas funiformis* AF24-28AC with a deposit number of GDMCC 60093, *Megamonas funiformis* DSM 19343 or *Megamonas funiformis* JCM 14723, or a combination thereof.

In a preferred embodiment, the composition is an oral preparation.

In a preferred embodiment, the administration dosage is 0.01 to 5 g/50 kg body weight per day, preferably 0.1 to 2 g/50 kg body weight per day.

In a preferred embodiment, the subject includes human or non-human mammals.

In a preferred embodiment, the non-human mammal includes rodents such as mice and rats, and primates such as monkey.

In a preferred embodiment, the method is non-diagnostic or non-therapeutic.

In a preferred embodiment, the metabolic disease comprises a lipid metabolism disease, a purine metabolism disease and/or an insulin metabolism disease.

In a preferred embodiment, the metabolic disease is selected from the group consisting of obesity, diabetes, atherosclerosis-related diseases, cardiovascular disease, hyperuricemia or a combination thereof.

In a preferred embodiment, the composition comprises: (a) a safe and effective amount of *Megamonas funiformis* and/or its metabolites, and (b) a food acceptable or pharmaceutically acceptable carrier.

In a preferred embodiment, the composition comprises $1 \times 10^{-1}$ to $1 \times 10^{20}$ cfu/mL or $1 \times 10^{-1}$ to $1 \times 10^{20}$ cfu/g of *Megamonas funiformis*, preferably $1 \times 10^{4}$ to $1 \times 10^{15}$ cfu/mL or $1 \times 10^{4}$ to $1 \times 10^{15}$ cfu/g of *Megamonas funiformis*, based on the total volume or total weight of the composition.

In a preferred embodiment, the composition further comprises probiotics and/or prebiotics.

In a preferred embodiment, the composition further comprises a substance capable of maintaining the vitality of *Megamonas funiformis*.

In a preferred embodiment, the composition is selected from the group consisting of a food composition, a health care composition, a pharmaceutical composition, a beverage composition, a feed composition, or a combination thereof.

In a seventh aspect, provided in embodiments is a method for achieving one or more activities from the group consisting of:
 (i) reducing a blood glucose level in mammals;
  (ii) ameliorating glucose intolerance in mammals;
  (iii) ameliorating myocardial ischemia in mammals;
  (iv) reducing a blood uric acid level in mammals;
  (v) reducing a blood lipid level in mammals;
  (vi) reducing body weight of mammals; and
  (vii) ameliorating vasculopathy in mammals,
by administering a *Megamonas funiformis* or a composition comprising the *Megamonas funiformis* to a subject in need.

*Megamonas funiformis* in the present disclosure shows significant efficacy on type II diabetes, capable of ameliorating symptoms such as high blood glucose and the like, and also capable of remarkably relieving the glucose intolerance of diabetes patients. *Megamonas funiformis* in the present disclosure can effectively reduce the serum cholesterol content, thus avoiding atherosclerosis and alleviating coronary heart disease. It is also found that *Megamonas funiformis* can effectively alleviate myocardial ischemic disease, such as reducing the ST-segment displacement of myocardial ischemia in mammals thus ameliorating vasculopathy through research of effect of *Megamonas funiformis* on experimental myocardial ischemia in rats. Meanwhile, *Megamonas funiformis* exhibits a significant alleviating effect on hyperuricemia, particularly manifested in significantly ameliorating the pathological conditions of patients with hyperuricemia and controlling the decrease of uric acid value. Therefore, the *Megamonas funiformis* of the present disclosure is useful in the preparation of a composition for preventing and/or treating metabolic diseases.

DETAILED DESCRIPTION

The present disclosure is further described in detail through specific embodiments in the below. In the following embodiments, many details are described in order to enable the present disclosure to be better understood. However, those skilled persons in the art can easily appreciated that some of the features can be omitted under different circumstances or can be replaced by other materials or methods.

Additionally, the features, operations or features described in the specification can be combined in any appropriate manner to constitute various implementations. Meanwhile, the steps or actions described in the method can also be sequentially exchanged or adjusted in a manner obvious to those skilled in the art. Therefore, the various sequences in the specification are only for clearly describing a certain embodiment and do not mean a necessary sequence, unless otherwise stated that a certain sequence is required to be followed.

After extensive and in-depth research and experiments, inventors of the present application unexpectedly discovered that *Megamonas funiformis* is capable of preventing and/or treating metabolic diseases (such as obesity, diabetes, atherosclerosis-related diseases, cardiovascular disease, hyperuricemia). Through administration of an active composition containing *Megamonas funiformis* to experimental subjects, it is discovered that the composition can significantly control the weight gain rate of subjects (such as mice), effectively slow down the weight gain of subjects (such as mice), effectively reduce blood glucose, effectively ameliorate glucose intolerance of diabetic subjects (such as mice), and effectively control the levels of TC, TG, LDLC in blood and blood viscosity, thereby reducing blood lipids and the indicators related to atherosclerosis-related diseases, thus having an excellent relieving and protecting effect on myocardial ischemia, and effectively reducing blood uric acid. Therefore, it is shown that *Megamonas funiformis* can effectively alleviate metabolic diseases (such as obesity, diabetes, atherosclerosis-related diseases, cardiovascular disease and hyperuricemia) or the like. On this basis, the present application is completed by the inventors.

As used herein, the terms "comprising", "including" or "containing" mean that various ingredients can be applied together in the mixture or composition of the present disclosure. Therefore, the terms "mainly consisting of" and "consisting of" are included in the scope of terms "comprising", "including" or "containing".

As used herein, the term "growth factor" includes a milk growth factor, specifically including nutrients of vitamins, purines, pyrimidines or a combination thereof. In which, the vitamins include but are not limited to Vitamin C, Vitamin E, Vitamin A, Vitamin A precursor, Vitamin $B_6$, Vitamin $D_3$, Vitamin K, folic acid or a combination thereof; the purines include but are not limited to purine nucleosides, which include 5'-phosphate esters of purine nucleosides; the 5'-phosphate esters of purine nucleosides are selected from the group consisting of inosinic acid (inosine-5'-phosphate ester; IMP), guanylic acid (guanosine-5'-phosphate ester; GMP), xanthylic acid (xanthine-5'-phosphate ester; XMP), adenylic acid (adenosine-5'-phosphate ester; AMP) or a combination thereof; the pyrimidines include all substances containing a pyrimidine structure.

As used herein, the terms "reducing the body weight of mammals", "controlling the weight gain of mammals" and "slowing down the weight gain of mammals" can be used interchangeably and refer to the treatment of weight gain symptoms caused by obesity.

As used herein, the term "ameliorating vasculopathy in mammals" refers to the treatment of symptoms of vasculopathy caused by atherosclerosis. In the present disclosure, ameliorating vasculopathy in mammals includes amelioration of one or more indicators selected from the group consisting of: blood viscosity, blood rheology, blood lipids (mainly triglyceride, total cholesterol, high-density lipoprotein and low-density lipoprotein), ST segment of electrocardiogram.

As used herein, the term "ST-segment displacement of myocardial ischemia" refers to that myocardial ischemia can be diagnosed by electrocardiography, mainly manifested as depression or elevation of ST-segment.

*Megamonas funiformis* and its Application

As used herein, the terms "strain *Megamonas funiformis*", "*Megamonas funiformis*" and "*Megamonas funiformis* of the present disclosure" can be used interchangeably. In a preferred embodiment, the strain is *Megamonas funiformis* AF24-28AC with a deposit number of GDMCC 60093, which is isolated from human feces, preferably a healthy female. The physiological characteristics of *Megamonas funiformis* is described as follows: the *Megamonas funiformis* AF24-28AC is isolated by using peptone yeast extract glucose (PYG) medium in an anaerobic condition at 37° C.; the colony of *Megamonas funiformis* AF24-28AC after culturing for 2 days in PYG medium is light yellow, flat, with irregular wavy edges and low water content, and about 2-3 mm in diameter; the mycelium under microscope is rod-shaped, Gram-negative, and does not produce spores and flagella; *Megamonas funiformis* AF24-28AC is detected to be negative to catalase and oxidase; *Megamonas funiformis* AF24-28AC can produce several carbohydrates after fermentation, including glucose, mannitol, lactose, sucrose, maltose, salicyl alcohol, xylose, arabinose, glycerol, cellobiose, mannitol, melezitose, raffinose, sorbitol, rhamnose and trehalose; can mainly produce acetic acid, propionic acid, isovaleric acid, benzoic acid and lactic acid; and can also produce a small amount of valeric acid, 3-methyl butyric acid, maleic acid, succinic acid, malic acid, adipic acid and citric acid. Moreover, the *Megamonas funiformis* AF24-28AC of the present disclosure is resistant to penicillin, oxacillin and cefoperazone, while it is sensitive to other 17 antibiotics in Table 2.

The present disclosure provides the application of *Megamonas funiformis* in the treatment and/or prevention of metabolic diseases (such as obesity, diabetes, atherosclerosis-related diseases, cardiovascular disease and hyperuricemia). Subjects (such as mice) having the similar body weight, age and the like are fed with high-fat diet and injected with streptase urea (STZ) to induce a type II diabetes (T2D) model. After intragastric administration of *Megamonas funiformis*, the subjects are observed on body weight, blood glucose and glucose tolerance to reflect the therapeutic effect of *Megamonas funiformis* on T2D. Through high-fat feeding subjects (such as mice) with the similar body weight, age and the like, the effect of *Megamonas funiformis* on serum cholesterol content under high-fat feeding conditions is investigated, so as to indirectly reflect the efficacy of *Megamonas funiformis* on atherosclerosis-related diseases. A hyperuricemia model is induced by administering a feed containing 5% oteracil potassium to subjects (such as mice) with the similar body weight, age and the like. After intragastric administration of *Megamonas funiformis*, the change of uric acid value of subjects is observed to reflect the therapeutic effect of *Megamonas funiformis* on hyperuricemia. It is found through the experimental results that *Megamonas funiformis* of the present disclosure can ameliorate a series of indicators related to metabolic diseases (such as obesity, diabetes, atherosclerosis-related diseases, cardiovascular disease, hyperuricemia), for example, significantly controlling the weight gain rate of subjects (such as mice), effectively slowing down the weight gain of subjects (such as mice), effectively reducing blood glucose level, effectively ameliorating glucose intolerance in subjects (such as mice) with diabetes, and effectively controlling the levels of TC, TG, LDLC in blood and blood viscosity, indicating the ability of *Megamonas funiformis* on reduction of blood lipids and indicators related to atherosclerosis-related diseases, remarkable relieving and protecting effect on myocardial ischemia, and effectively decrease of blood uric acid. Therefore, *Megamonas funiformis* of the present disclosure can effectively alleviate metabolic diseases (such as obesity, diabetes, atherosclerosis-related diseases, cardiovascular disease, hyperuricemia) and the like.

Composition and its Application

The *Megamonas funiformis* of the present disclosure can be useful in the preparation of a composition for treating and/or preventing metabolic diseases. Preferably, the composition includes a food composition, a health care composition, a pharmaceutical composition, a beverage composition or a feed composition. More preferably, the composition is a pharmaceutical composition. The composition contains an effective amount of *Megamonas funiformis*. In a preferred embodiment, the composition further contains a growth factor, such as a milk growth factor. In a preferred embodiment, the composition further contains probiotics selected from the group consisting of Lactic acid bacteria, *Bifidobacteria, Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Megamonas funiformis* (such as a protective agent), which includes cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof. The substance capable of maintaining the viability of *Megamonas funiformis* (such as a protective agent) is of a weight ratio of 0.1% to 2%, preferably 0.5% to 1.5%, more preferably 0.5% to 1.0%, based on the total weight of the composition. In a preferred embodiment, the composition is a liquid preparation, a solid preparation or a semi-solid preparation. In a preferred embodiment, the liquid preparation is selected from the group consisting of a solution product or a suspension product. In a preferred embodiment, the dosage form of the composition is selected from the group consisting of powder, pulvis, tablet, sugar coating agent, capsule, granule, suspension, solution, syrup, drop, sublingual tablet or a combination thereof.

The composition of the present disclosure may be administered in any form of oral solution, tablet, injection, orally disintegrating tablet, lyophilized powder or capsule, preferably in the dosage form of enteric agent (such as capsule). In the present disclosure, the excipient, pharmaceutically acceptable vehicle and carrier used in the present disclosure are mainly selected depending on the property suitable for the bacteria or metabolites thereof and the specific administration means required, which is beneficial to the smooth passage of the bacteria or metabolites thereof through stomach thus absorbed by the administered subject, unless especially indicated. These substances can be selected according to the administration routes.

The composition of the present disclosure may further contain any additional excipients commonly used in a pharmaceutical preparation, for example, for stabilization of the composition itself, or allowing to be easily dispersed or imparting a suitable taste. Among the excipients, suitable examples are inulin, fructose, starch, xylooligosaccharide, silicon dioxide, buffering agent and flavoring agent.

Lactose, maltodextrin, glucose, sucrose, sorbitol, mannose, starch, arabic gum, calcium phosphate, alginate, gelatin, calcium silicate, fine crystalline cellulose, polyvinylpyrrolidone (PVP), cellulose, water, syrup, methyl cellulose, methyl hydroxybenzoate, propyl hydroxybenzoate, talc, magnesium stearate, mineral oil and the like can be all used as carriers, excipients, diluents and the like of the pharmaceutical composition of the present disclosure.

Further, the pharmaceutical composition of the present disclosure may further contain lubricant, wetting agent, emulsifier, suspension stabilizer, preservative, sweetening agent, flavor and the like. The pharmaceutical composition of the present disclosure can be produced in an enteric coating preparation via a variety of well-known methods, so that the active component of the pharmaceutical composition (i.e., the microorganism) can pass through stomach smoothly without destroyed by gastric acid.

Further, the microorganism of the present disclosure may be used in the form of capsule prepared by conventional methods. For example, standard excipients and lyophilized microorganism of the present disclosure are mixed to obtain pills which are subsequently dispensed into gelatin capsules. In addition, the microorganism of the present disclosure and pharmaceutically acceptable excipients (such as liquid gum, cellulose, silicate, mineral oil and the like) can be mixed and prepared into a suspension liquid or a dispersion liquid, and such a suspension or dispersion liquid can be filled into soft gelatin capsules.

The pharmaceutical composition of the present disclosure can be prepared into enteric coating tablets for oral use. The term "enteric coating" in the present disclosure includes all coatings that are allowed for conventional drugs. These coatings are not degraded by gastric acid, however, can be completely broken down in small intestine and then quickly release the microorganism of the present disclosure. The enteric coating of the present disclosure can be maintained in an HCl solution suitable for gastric acid synthesis (such as pH=1) at 36° C. to 38° C. for more than 2 hours, preferably broken down in a buffer solution suitable for intestinal fluid synthesis (such as pH=7.0) within one hour.

The enteric coating of the present disclosure is coated in an amount of about 16 to 30 mg per tablet, preferably 16 to 25 mg per tablet, and more preferably 16 to 20 mg per tablet. The thickness of the enteric coating in the present disclosure is 5 to 100 μm, ideally 20 to 80 μm. The components of enteric coating are selected from conventional polymers which are known in public.

The preferred enteric coating of the present disclosure is prepared by a copolymer of cellulose acetate phthalate polymer (or cellulose acetate trimellitate polymer) and methacrylic acid, for example, a copolymer of methacrylic acid (in an amount of 40% or above) and methylcellulose hydroxypropyl phthalate or its ester derivatives.

The cellulose acetate phthalate used in the enteric coating of the present disclosure has a viscosity of about 45 to 90 cp, an acetyl content of 17 to 26%, and a phthalic acid content of 30 to 40%. The cellulose acetate trimellitate used in the enteric coating has a viscosity of about 5 to 21 cp, and an acetyl content of 17 to 26%. Cellulose acetate trimellitate, produced by Eastman Kodak Company, can be used as the enteric coating material in the present disclosure.

The hydroxypropyl methylcellulose phthalate used in the enteric coating of the present disclosure generally has a molecular weight of 20,000 to 130,000 Daltons (ideally 80,000 to 100,000 Daltons), a hydroxypropyl content of 5 to 10%, a methoxyl content of 18 to 24% and a phthaloyl content of 21 to 35%.

The hydroxypropyl methylcellulose phthalate used in the enteric coating of the present disclosure is HP50, produced by Shin-Etsu Chemical Co. Ltd. of Japan. HP50 contains 6 to 10% of hydroxypropyl, 20 to 24% of methoxy and 21 to 27% of propyl, with a molecular weight of 84,000 Daltons. Another enteric coating material is HP55, which contains 5 to 9% of hydroxypropyl, 18 to 22% of methoxy and 27 to 35% of phthalic acid, with a molecular weight of 78,000 Daltons.

The enteric coating of the present disclosure is prepared by spraying an enteric coating solution onto a core through conventional methods. Solvents for the enteric coating are alcohols (such as ethanol), ketones (such as acetone), halogenated hydrocarbon compounds (such as dichloromethane) or a combination thereof. Softeners such as di-n-butyl phthalate and glyceryl triacetate are added to the enteric coating solution in a ratio of 1 part of the coating to about 0.05 parts (or about 0.3 parts) of the softener. The spraying method is preferably performed continuously, and the amount of spray material can be controlled according to the conditions for coating. The spray pressure can be adjusted flexibly, generally an average pressure of 1 to 1.5 Pa will generate ideal results.

The "pharmaceutically effective amount" or "safe and effective amount" in the specification refers to an amount which is functional or active to human and/or animals and is acceptable to human and/or animals. For example, a preparation containing $1 \times 10$-$1 \times 10^{15}$ cfu/ml or cfu/g (particularly $1 \times 10^4$-$1 \times 10^{10}$ cfu/ml or cfu/g, more particularly $1 \times 10^6$-$1 \times 10^{10}$ cfu/ml or cfu/g) of *Megamonas funiformis* and/or metabolites thereof can be prepared in the present disclosure.

When the *Megamonas funiformis* is used in the manufacture of a pharmaceutical composition, the effective dosage of *Megamonas funiformis* or metabolites thereof used may vary depending on the administration route and the severity of disease to be treated. A dosage form suitable for internal administration includes about $1 \times 10$-$1 \times 10^{15}$ cfu/ml or cfu/g (preferably $1 \times 10^4$-$1 \times 10^{10}$ cfu/ml or cfu/g, more preferably $1 \times 10^6$-$1 \times 10^{10}$ cfu/ml or cfu/g) of active *Megamonas funiformis* or its active component produced by fermentation, which is closely mixed with a solid or liquid pharmaceutically acceptable carrier. This dosage regimen can be adjusted to provide the best therapeutic response. For example, several divided doses may be administered daily or the dosage may be proportionally reduced according to the urgent need of treatment condition.

The *Megamonas funiformis* or metabolites thereof may be administered by oral route or the like. Solid carriers include starch, lactose, dicalcium phosphate, microcrystalline cellulose, sucrose and white clay; and liquid carriers include culture medium, polyethylene glycol, non-ionic surfactants and edible oils (such as corn oil, peanut oil and sesame oil), as long as they are suitable for the property of *Megamonas funiformis* or metabolites thereof and the specific administration means required. Adjuvants commonly used in the manufacture of a pharmaceutical composition may also be advantageously included, for example, flavoring agents, pigments, preservatives and antioxidants such as Vitamin E, Vitamin C, BHT and BHA.

From the standpoint of ease of manufacture and administration, the preferred pharmaceutical composition is a solid composition, especially tablets and/or solid-filled or liquid-filled capsules. Preferred is oral administration.

The composition of the present disclosure is administered to individuals (a subject, an experimental subject) once or several times per day. The dosage unit of administration refers to a dosage that can be physically separated and suitable for application in human or all individuals of other mammals. Each unit contains a pharmaceutically acceptable carrier and a therapeutically effective amount of microorganism of the present disclosure. The administration dosage varies with the body weight of patient and the severity of metabolic disease (such as obesity, diabetes, atherosclerosis-related diseases, cardiovascular disease and hyperuricemia), the contained supplementary active components and the microorganism used. Further, if possible, the composition can be administered separately and continuously as necessary. Therefore, the administration dosage does not limit the scope of the present disclosure. In addition, the "composition" in the present disclosure means not only a medicament but also a functional food and a health supplement food. In a preferred embodiment, the composition includes beverage, food, medicine, animal feed or the like.

In a preferred embodiment, the present disclosure further provides a food composition, which contains an effective amount of *Megamonas funiformis* and/or metabolites thereof as well as a food acceptable carrier as balance. The dosage form of the food composition is selected from a solid product, a dairy product, a solution product, a powder product or a suspension product. In a preferred embodiment, the food composition may further contain a growth factor, such as a milk growth factor. In a preferred embodiment, the composition further contains probiotics selected from the group consisting of Lactic acid bacteria, *Bifidobacteria*, *Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Megamonas funiformis* (such as a protective agent), including cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof.

In a preferred embodiment, the composition has the following formula:
  $1 \times 10$-$1 \times 10^{15}$ cfu/mL of *Megamonas funiformis* and/or metabolites thereof; and
  a food acceptable or pharmaceutically acceptable carrier and/or excipient.

In another preferred embodiment, the composition has the following formula:
  $1 \times 10^4$-$1 \times 10^{10}$ cfu/mL of *Megamonas funiformis* and/or metabolites thereof; and
  a food acceptable or pharmaceutically acceptable carrier and/or excipient.

Microecological Preparation

Microecological preparation is a biological preparation containing probiotics and metabolites thereof or a dietary supplement that can supply probiotics, which are capable of adjusting and maintaining the microecological balance in intestine, thus achieving the purpose of improving human health. The microecological preparation mainly includes probiotics, prebiotics and synbiotics.

In the present disclosure, the microecological preparation contains (a) a safe and effective amount of *Megamonas funiformis* and/or metabolites thereof; and (b) a food acceptable or pharmaceutically acceptable carrier. In a preferred embodiment, the preparation further contains a growth factor, such as a milk growth factor, preferably including vitamins, purines and/or pyrimidines. In a preferred embodiment, the preparation further contains probiotics selected from the group consisting of Lactic acid bacteria, *Bifidobacteria, Lactobacillus acidophilus* or a combination thereof; and/or prebiotics selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof. In a preferred embodiment, the composition further contains a substance capable of maintaining the viability of *Megamonas funiformis* (such as a protective agent) selected from the group consisting of cysteine, glutathione, butyl hydroxyanisole, dibutylmethyltoluene, tocopherol, antioxidant of bamboo leaf, D-isoascorbic acid and sodium salt thereof, sodium ascorbate, calcium ascorbate, phospholipid, Vitamin C (ascorbic acid), Vitamin E or a combination thereof.

Method for Producing *Megamonas funiformis*

Generally, *Megamonas funiformis* can be produced by conventional methods.

In the present disclosure, provided is a method capable of producing *Megamonas funiformis* on a large scale. In particular, the method includes steps of:
  (a) culturing the *Megamonas funiformis* of the present disclosure under a condition suitable for culturing, thereby obtaining a culture product;
  (b) optionally, isolating *Megamonas funiformis* bacterial cells and/or metabolites thereof from the culture product; and
  (c) optionally, mixing the culture product obtained in (a) or the *Megamonas funiformis* bacterial cells and/or metabolites thereof obtained in (b) with a food acceptable or pharmaceutically acceptable carrier, thereby obtaining a composition.

In the present disclosure, the condition suitable for culturing refers to any conditions suitable for culturing *Megamonas funiformis* of the present disclosure. In a preferred embodiment, the condition suitable for culturing refers to anaerobic culturing with PYG medium at 37° C. for 24 to 72 hours.

Method of Reducing a Blood Glucose Level in Mammals

In a preferred embodiment, the method of reducing a blood glucose level in mammals includes: administering the *Megamonas funiformis*, the pharmaceutical composition, the food composition, the beverage composition or a combination thereof of the present disclosure to a subject. The subject includes mammals, such as human.

In a preferred embodiment, the method of reducing a blood glucose level in mammals includes: administering the *Megamonas funiformis*, the pharmaceutical composition, the food composition, the animal feed or a combination thereof of the present disclosure to a subject. The subject includes animals, preferably a murine or a rabbit.

Method of Ameliorating Glucose Intolerance in Mammals

In a preferred embodiment, the method of ameliorating glucose intolerance in mammals includes: administering the *Megamonas funiformis*, the pharmaceutical composition, the food composition, the beverage composition or a combination thereof of the present disclosure to a subject. The subject includes mammals, such as human.

In a preferred embodiment, the method of ameliorating glucose intolerance in mammals includes: administering the *Megamonas funiformis*, the pharmaceutical composition, the food composition, the animal feed or a combination thereof of the present disclosure to a subject. The subject includes animals, preferably a murine or a rabbit.

Method of Ameliorating Myocardial Ischemia in Mammals

In a preferred embodiment, the method of ameliorating myocardial ischemia in mammals includes: administering the *Megamonas funiformis*, the pharmaceutical composition, the food composition, the beverage composition or a combination thereof of the present disclosure to a subject. The subject includes mammals, such as human.

In a preferred embodiment, the method of ameliorating myocardial ischemia in mammals includes: administering the *Megamonas funiformis*, the pharmaceutical composition, the food composition, the animal feed or a combination thereof of the present disclosure to a subject. The subject includes animals, preferably a murine or a rabbit.

Method of Reducing a Blood Uric Acid Level in Mammals

In a preferred embodiment, the method of reducing a blood uric acid level in mammals includes: administering the *Megamonas funiformis*, the pharmaceutical composition, the food composition, the beverage composition or a combination thereof of the present disclosure to a subject. The subject includes mammals, such as human.

In a preferred embodiment, the method of reducing a blood uric acid level in mammals includes: administering the *Megamonas funiformis*, the pharmaceutical composition, the food composition, the animal feed or a combination thereof of the present disclosure to a subject. The subject includes animals, preferably a murine or a rabbit.

Method of Reducing a Blood Lipid Level in Mammals

In a preferred embodiment, the method of reducing a blood lipid level in mammals includes: administering the *Megamonas funiformis*, the pharmaceutical composition, the food composition, the beverage composition or a combination thereof of the present disclosure to a subject. The subject includes mammals, such as human.

In a preferred embodiment, the method of reducing a blood lipid level in mammals includes: administering the *Megamonas funiformis*, the pharmaceutical composition, the food composition, the animal feed or a combination thereof of the present disclosure to a subject. The subject includes animals, preferably a murine or a rabbit.

Method of Reducing Body Weight of Mammals

In a preferred embodiment, the method of reducing body weight of mammals includes: administering the *Megamonas funiformis*, the pharmaceutical composition, the food composition, the beverage composition or a combination thereof of the present disclosure to a subject. The subject includes mammals, such as human.

In a preferred embodiment, the method of reducing body weight of mammals includes: administering the *Megamonas funiformis*, the pharmaceutical composition, the food composition, the animal feed or a combination thereof of the present disclosure to a subject. The subject includes animals, preferably a murine or a rabbit.

Method of Ameliorating Vasculopathy in Mammals

In a preferred embodiment, the method of ameliorating vasculopathy in mammals includes: administering the *Megamonas funiformis*, the pharmaceutical composition, the food composition, the beverage composition or a combination thereof of the present disclosure to a subject. The subject includes mammals, such as human.

In a preferred embodiment, the method of ameliorating vasculopathy in mammals includes: administering the *Megamonas funiformis*, the pharmaceutical composition, the food composition, the animal feed or a combination thereof of the present disclosure to a subject. The subject includes animals, preferably a murine or a rabbit.

Method of Preventing and/or Treating Metabolic Diseases

In a preferred embodiment, the method of preventing and/or treating metabolic diseases includes: administering the *Megamonas funiformis*, the pharmaceutical composition, the food composition, the beverage composition or a combination thereof of the present disclosure to a subject. The subject includes mammals, such as human.

In a preferred embodiment, the method of preventing and/or treating metabolic diseases includes: administering the *Megamonas funiformis*, the pharmaceutical composition, the food composition, the animal feed or a combination thereof of the present disclosure to a subject. The subject includes animals, preferably a murine or a rabbit.

Deposit of Microorganism

The strain *Megamonas funiformis* AF24-28AC of the present disclosure was deposited at Guangdong Microbial Culture Collection Center (GDMCC, fifth floor of No. 59 Building, 100 Xianlie Middle Road, Guangzhou) on Oct. 13, 2016, with a deposit number of GDMCC 60093 and a deposit name of *Megamonas funiformis* AF24-28AC.

The present disclosure mainly has the following advantages:

(a) the *Megamonas funiformis* of the present disclosure can significantly treat and/or prevent metabolism related diseases, such as obesity, diabetes, atherosclerosis-related diseases, cardiovascular disease, hyperuricemia or the like.

(b) the *Megamonas funiformis* of the present disclosure can significantly reduce body weight and blood lipids, such as lowering levels of total cholesterol, triglyceride, low-density lipoprotein, and blood viscosity.

(c) the *Megamonas funiformis* of the present disclosure can significantly ameliorate myocardial ischemia and vasculopathy.

(d) the *Megamonas funiformis* of the present disclosure can significantly reduce blood glucose and ameliorate glucose intolerance in mammals.

(e) the *Megamonas funiformis* of the present disclosure can significantly reduce blood uric acid level.

(f) the *Megamonas funiformis* of the present disclosure exhibits significant efficacy, nearly without toxic and side effects, thus greatly reducing the treatment cost.

The present disclosure is further described as below with reference to specific embodiments. It should be understood that these examples are only for illustrating the present disclosure and not intended to limit the scope of the present disclosure. The conditions of experimental methods not specifically indicated in the following examples are usually in accordance with conventional conditions as described in Sambrook et al., Molecular Cloning: A Laboratory Manual (New York: Cold Spring Harbor Laboratory Press, 1989), or according to the conditions described in the Journal of Microbiology: An Experimental Handbook (edited by James Cappuccino and Natalie Sherman, Pearson Education Press) or the manufacturer's proposed conditions.

Unless otherwise specified, the materials and agents used in the examples are all commercially available products.

Example 1 Isolation and Identification of *Megamonas funiformis* AF24-28AC

The sample to be isolated was obtained from faeces of a healthy female, which was subjected to isolation by a spread plate method in gradient dilution. The plates were cultured by PYG medium (purchased from Huankai Microbial Technology Co., Ltd.) in an anaerobic condition (anaerobic gas components: $N_2:CO_2:H_2=90:5:5$) for 48 hours. Single colonies were picked out and purified by streaking to obtain a pure culture of each single colony.

The genomic DNA of isolated bacteria was extracted, followed by PCR amplification using 16S rDNA universal primer 27f (5'-AGAGTTTGATCATGGCTCAG-3', SEQ ID NO.: 2) and primer 1492r (5'-TAGGGTTACCTTGT-TACGACTT-3', SEQ ID NO.:3). The amplification condition was as below: 94° C. for 4 minutes; 20 cycles for 94° C. 30 s, 65° C.–57° C. 40 s and 72° C. 90 s; 10 cycles for 94° C. 30 s, 57° C. 40 s and 72° C. 90 s; 72° C. for 10 minutes; holding at 4° C.

The obtained 16S rDNA amplification product was subjected to electrophoretic detection, purification and 3730 sequencing to obtain a 16S rDNA sequence (SEQ ID NO.: 1). The 16S rDNA sequence of strain AF24-28AC was subjected to alignment based on EzBioCloud database (http://www.ezbiocloud.net/identify). It is found that strain *Megamonas funiformis* (*Megamonas funiformis* DSM 19343, purchased from the Deutsche Sammlung von Mikroorganismen and Zellkulturen, DSMZ) has the highest homology (i.e., 99.09%) with the AF24-28AC. Thus, it can be substantively identified that the strain AF24-28AC belongs to species *Megamonas funiformis*.

1.1 Physiological and Biochemical Characteristics of AF24-28AC

The colony characteristics of isolated AF24-28AC after culturing for 48 hours in PYG medium is light yellow, flat, with irregular wavy edges and low water content, and about 2-3 mm in diameter. The mycelium under microscope is rod-shaped, Gram-negative, and does not produce spores and flagella. The AF24-28AC was detected to be negative to catalase and oxidase. The AF24-28AC on carbon source utilization was detected by API 20A (Mérieux, France), with results shown in Table 1, in which "+" indicates a positive reaction, "−" indicates a negative reaction and "w" indicates a weak positive reaction.

TABLE 1

| Nos. | Reaction | Result |
|---|---|---|
| 1 | production of indole | − |
| 2 | urea (urease) | − |
| 3 | glucose | + |
| 4 | mannitol | + |
| 5 | lactose | + |
| 6 | sucrose | + |
| 7 | maltose | + |
| 8 | salicyl alcohol | + |
| 9 | xylose | + |
| 10 | arabinose | + |
| 11 | Gelatin hydrolysis | − |

TABLE 1-continued

| Nos. | Reaction | Result |
|---|---|---|
| 12 | Esculin | − |
| 13 | glycerin | + |
| 14 | cellobiose | w |
| 15 | mannose | + |
| 16 | melezitose | w |
| 17 | raffinose | + |
| 18 | sorbitol | + |
| 19 | rhamnose | w |
| 20 | trehalose | + |

1.2 Antibiotic Sensitivity of AF24-28AC

The sensitivity of AF24-28AC to 20 common antibiotics was tested by the drug sensitive paper method. 100 μl of AF24-28AC bacterial solution cultured to the logarithmic phase was spread plated. Antibiotic susceptibility papers (purchased from Hangzhou Microbial Reagent Co. LTD) were affixed on the medium surface of plates, cultured at 37° C. for 48 hours, after which the size of inhibition zone was measured. The results are shown in Table 2.

TABLE 2

| Antibiotics | Diameter of inhibition zone (cm) | Antibiotics | Diameter of inhibition zone (cm) |
|---|---|---|---|
| Penicillin | 0.0 | Ceftriaxone Sodium | 1.0 |
| Oxacillin | 0.0 | Cefoperazone | 0.0 |
| Ampicillin | 1.0 | Amikacin Δ | 2.6 |
| Carbenicillin | 1.2 | Gentamicin | 1.7 |
| Kanamycin | 1.8 | Fortum (Ceftazidime) Δ | 2.0 |
| Cefalexin | 2.2 | Neomycin | 1.3 |
| Cefazolin | 4.0 | Tetracycline | 4.2 |
| Cefradine | 0.8 | Doxycycline | 4.0 |
| Piperacillin | 1.2 | Minocin (Minocycline) Δ | 4.0 |
| Cefuroxime | 3.8 | Erythromycin | 1.3 |

The results show that the AF24-28AC is resistant to penicillin, oxacillin and cefoperazone, and is sensitive to other 17 antibiotics.

Example 2 Bioactive Components of *Megamonas funiformis* AF24-28AC

This example mainly examined the generation of metabolites of AF24-28AC after culturing in PYG culture for 48 hours, mainly including the content of short-chain fatty acids (SCFAs) and organic acids. SCFAs mainly include acetic acid, propionic acid, butyric acid and valeric acid. Organic acids include 3-methyl butyric acid, quinic acid, lactic acid, oxalic acid, malonic acid, benzoic acid, maleic acid, succinic acid, trans-fumaric acid, malic acid, adipic acid, tartaric acid, shikimic acid, citric acid, isocitric acid and L-ascorbic acid. The standards of each SCFAs and organic acids are purchased from Sigma. The detection procedure is as follows.

2.1 Sample Pretreatment 1 ml of AF24-28AC bacterial solution was taken for centrifugation at 12000 r/min for 5 minutes, and the supernatant was collected for detection of short-chain fatty acids (SCFAs) and organic acids.

2.2 Determination of SCFAs

The SCFAs were detected by using the gas chromatograph of Agilent (GC-7890B, Agilent), in which the capillary column (30 m×0.25 mm×0.25 μm) from HP-INNOWax (Cross-Linked PEG) was selected for analysis, and the detector was a hydrogen flame ion detector.

The parameters of the GC were set as follows: column temperature of 180~200° C.; gasification chamber temperature of 240° C.; detection temperature of 210° C.; injection volume of 2 μl; flow rate of carrier gas: $N_2$, 50 ml/min; hydrogen flow rate of 50 ml/min; and air flow rate of 600~700 ml/min.

2.3 Determination of Organic Acids

The organic acids were also detected by the gas chromatograph of Agilent (GC-7890B, Agilent). 122-5532G DB-5 ms column (40 m×0.25 mm×0.25 μm) is used, in which column temperature is 270~290° C., inlet temperature is 250° C. and gas flow rate is 0.86 ml/min.

2.4 Experimental Results

TABLE 3

| | Products | | | | |
|---|---|---|---|---|---|
| | acetic acid | formic acid | propionic acid | iso-butyric acid | butyric acid |
| Content (mmol/L) | 23.75 | 0 | 48.29 | 0 | 0 |

| | Products | | | | |
|---|---|---|---|---|---|
| | isovaleric acid | valeric acid | benzoic acid | 3-methyl butyric acid | quinic acid |
| Content (mmol/L) | 1.14 | 0.74 | 3.47 | 0.37 | 0 |

| | Products | | | | |
|---|---|---|---|---|---|
| | lactic acid | oxalic acid | malonic acid | maleic acid | succinic acid |
| Content (mmol/L) | 33.62 | 0 | 0 | 0.04 | 0.06 |

| | Products | | | | |
|---|---|---|---|---|---|
| | trans-fumaric acid | malic acid | adipic acid | tartaric acid | shikimic acid |
| Content (mmol/L) | 0 | 0.02 | 0.23 | 0 | 0 |

| | Products | | |
|---|---|---|---|
| | citric acid | D, L-isocitric acid trisodium salt | L-Vitamin C |
| Content (mmol/L) | 0.13 | 0 | 0 |

The results in Table 3 show that the AF24-28AC is capable of producing acetic acid, propionic acid, isovaleric acid, benzoic acid and lactic acid, and can also produce a small amount of valeric acid, 3-methyl butyric acid, maleic acid, succinic acid, malic acid, adipic acid and citric acid.

The information of stains used in the following examples is described as follows.

The *Megamonas funiformis* AF24-28AC, DSM 19343, JCM 14723 were cultured by using PYG medium in an anaerobic condition at 37° C. The colony of *Megamonas funiformis* AF24-28AC after culturing for 2 days in PYG medium is light yellow, flat, with irregular wavy edges and low water content, and about 2-3 mm in diameter. The mycelium under microscope is rod-shaped, Gram-negative, and does not produce spores and flagella.

The strain *Megamonas funiformis* AF24-28AC of the present disclosure was deposited at Guangdong Microbial Culture Collection Center (GDMCC, fifth floor of No. 59 Building, 100 Xianlie Middle Road, Guangzhou) on Oct. 13, 2016, with a deposit number of GDMCC 60093 and a deposit name of *Megamonas funiformis* AF24-28AC.

The strain *Megamonas funiformis* DSM 19343 of the present disclosure was purchased from the Deutsche Sammlung von Mikroorganismen and Zellkulturen (DSMZ).

The strain *Megamonas funiformis* JCM 14723 of the present disclosure was purchased from the Japan Collection of Microorganisms (JCM).

TABLE 4

Strain information

| Nos. | Name of strain |
|---|---|
| Bacterial agent 1 | *Megamonas funiformis* DSM 19343 |
| Bacterial agent 2 | *Megamonas funiformis* AF24-28AC |
| Bacterial agent 3 | *Megamonas funiformis* JCM 14723 |

Example 3 Efficacy of *Megamonas funiformis* in an Obesity Animal Model

The obesity animal model is constructed by using C57BL/6 male mice (purchased from Guangdong Medical Experimental Animal Center) at 8 weeks old and 20±2 g of body weight, which is housed in a specific pathogen free (SPF) environment and access to food and water ad lib. The mice are randomly divided into 5 groups, with 10 mice in each group.

Control group: mice were fed with ordinary maintenance feed every day;

Bacterial agent group 1: mice were fed with high-fat feed every day, in which the DSM 19343 bacterial solution ($1\times10^8$ cfu/ml) was administered by gavage for 9 weeks after 4 weeks of feeding high-fat feed;

Bacterial agent group 2: mice were fed with high-fat feed every day, in which the AF24-28AC bacterial solution ($1\times10^8$ cfu/ml) was administered by gavage for 9 weeks after 4 weeks of feeding high-fat feed;

Bacterial agent group 3: mice were fed with high-fat feed every day, in which the JCM 14723 bacterial solution ($1\times10^8$ cfu/ml) was administered by gavage for 9 weeks after 4 weeks of feeding high-fat feed;

Obesity model group: mice were fed with high-fat feed every day, in which the culture medium in a same amount was administered by gavage for 9 weeks after 4 weeks of feeding high-fat feed.

During the experimental period, experimental data such as the body weight, body condition and food intake amount of mice were recorded every week. After the completion of experiment, the mice were sacrificed, and the fat weight was recorded and the serum was collected for detecting blood lipids by using the Elisa kit.

TABLE 5

Weight gain of mice in each group before and after administration of *Megamonas funiformis* by gavage

| Groups | Week 1 (g) | Week 3 (g) | Week 5 (g) | Week 7 (g) | Week 9 (g) |
|---|---|---|---|---|---|
| Control group | 20.35 | 21.11 | 21.98 | 22.87 | 23.90 |
| Bacterial agent group 1 | 22.34 | 23.57 | 24.66 | 25.23 | 25.97* |
| Bacterial agent group 2 | 22.45 | 23.44 | 24.98 | 25.11 | 25.57* |
| Bacterial agent group 3 | 21.36 | 23.65 | 24.58 | 25.14 | 25.45* |
| Obesity model group | 22.49 | 23.99 | 24.87 | 26.53 | 28.57 |

The results in Table 5 show that the body weight of mice increases gradually as the experiment progresses, in which the administration of *Megamonas funiformis* by gavage after feeding with high-fat feed can significantly control the weight gain rate of mice through the results of the obesity model group and Bacterial agent groups 1, 2 and 3, indicating *Megamonas funiformis* can effectively slow down the weight gain of obesity mice model (relative to model group, *P<0.05).

Example 4 Efficacy of *Megamonas funiformis* in a Diabetes Animal Model

The T2D animal model is constructed by using C57bL/6 mice (purchased from Guangdong Medical Experimental Animal Center) at 8 weeks old and 20±2 g of body weight. The mice are housed in a specific pathogen free (SPF) environment and adaptively fed for 1 week, followed by grouping and modeling. The T2D animal model is induced by injection of streptozotocin (STZ) along with feeding high-fat feed, and the mice having a fasting blood glucose (FBG) reaching 10 mM/L can be used as a T2D mice model. Fifty mice selected for experiments are randomly divided into 5 groups.

Model group: the T2D mice model was administered with saline solution by gavage;

Bacterial agent group 1: the T2D mice model was administered with the DSM 19343 bacterial solution ($1\times10^8$ cfu/ml) by gavage;

Bacterial agent group 2: the T2D mice model was administered with the AF24-28AC bacterial solution ($1\times10^8$ cfu/ml) by gavage;

Bacterial agent group 3: the T2D mice model was administered with the JCM 14723 bacterial solution ($1\times10^8$ cfu/ml) by gavage;

Metformin treatment group: the T2D mice model was treated with the positive drug metformin.

The experiment was carried out based on the different groups. After the construction of T2D mice model (i.e., FBG>10), the treatment was started and lasted for 2 months. The food intake amount and body weight of mice were recorded daily. Blood of mice was collected from the tail vein every week for detection of fasting blood glucose. The oral glucose tolerance test (OGTT) of mice was measured at week 4 of treatment and at the end of the experiment.

TABLE 6

Table of weight change

| Groups | Week 1 (g) | Week 3 (g) | Week 5 (g) | Week 7 (g) | Week 9 (g) |
|---|---|---|---|---|---|
| Model group | 21.86 | 23.65 | 27.92 | 29.33 | 31.12 |
| Bacterial agent group 1 | 22.34 | 23.57 | 24.26 | 25.53 | 25.97* |

TABLE 6-continued

Table of weight change

| Groups | Week 1 (g) | Week 3 (g) | Week 5 (g) | Week 7 (g) | Week 9 (g) |
|---|---|---|---|---|---|
| Bacterial agent group 2 | 21.45 | 22.44 | 23.98 | 25.03 | 25.57* |
| Bacterial agent group 3 | 21.96 | 23.25 | 24.48 | 25.12 | 25.45* |
| Metformin treatment group | 20.33 | 22.36 | 24.33 | 25.86 | 26.53* |

The results in Table 6 show that the body weight of mice increases gradually as the experiment progresses, in which the weight gain of mice in the Bacterial agent groups 1, 2 and 3 as well as the metformin treatment group is lower than that of mice in the model group, indicating that *Megamonas funiformis* can effectively slow down the weight gain of T2D mice model (relative to model group, *P<0.05/**P<0.01). Meanwhile, *Megamonas funiformis* has a more effective efficacy on controlling weight gain of T2D mice than the metformin.

TABLE 7

Experimental results of effect of *Megamonas funiformis* on fasting blood glucose in mice model

| Groups | Week 1 (mmol/L) | Week 3 (mmol/L) | Week 5 (mmol/L) | Week 7 (mmol/L) | Week 9 (mmol/L) |
|---|---|---|---|---|---|
| Model group | 16.5 | 17.1 | 17.8 | 17.3 | 16.4 |
| Bacterial agent group 1 | 15.9 | 15.5 | 13.6* | 10.8** | 8.7** |
| Bacterial agent group 2 | 16.4 | 15.9 | 14.9 | 11.5* | 8.9** |
| Bacterial agent group 3 | 15.9 | 15.5 | 13.8* | 10.5** | 7.9** |
| Metformin treatment group | 16.9 | 16.0 | 14.3 | 11.6* | 10.3** |

The results in Table 7 show that the fasting blood glucose level of mice in the bacterial agent groups 1, 2 and 3 as well as the metformin treatment group gradually decreases as the treatment progresses, thus the blood glucose level of the mice tends to be normal, with significant hypoglycemic effect. This indicates that the bacterial agent groups 1, 2 and 3 can effectively reduce blood glucose compared to the model group (*P value<0.05/**P<0.01). Meanwhile, the fasting blood glucose level of mice in the bacterial agent groups 1, 2 and 3 is lower than that of mice in the metformin treatment group, indicating that *Megamonas funiformis* has a better efficacy on decreasing fasting blood glucose than metformin.

TABLE 8

Effect of *Megamonas funiformis* on glucose tolerance in mice model

| Groups | 0 minute | 30 minutes | 60 minutes | 90 minutes | 120 minutes |
|---|---|---|---|---|---|
| Model group | 15.9 | 22.8 | 16.9 | 15.6 | 15.1 |
| Bacterial agent group 1 | 9.5 | 17.9 | 15.2 | 11.9* | 10.0* |
| Bacterial agent group 2 | 9.1 | 17.6 | 14.8 | 11.5* | 9.8* |
| Bacterial agent group 3 | 9.6 | 18.2 | 15.5 | 11.8* | 10.1* |
| Metformin treatment group | 9.3 | 19.4 | 16.6 | 11.7* | 10.4* |

The results of oral glucose tolerance test (OGTT) for mice shown in Table 8 indicate that the blood glucose of mice reaches the highest level (i.e., 17.6-22.8 mmol/L) at 30 minutes upon administration of glucose by gavage. The blood glucose level of mice in the bacterial agent groups 1, 2 and 3 as well as the metformin treatment group uniformly decreased, and reached to 10.0 mmol/L, 9.8 mmol/L, 10.1 mmol/L as well as 10.4 mmol/L at 120 minutes, whereas the blood glucose of mice in the model group is 15.1 mmol/L at 120 minutes, meaning that the blood glucose level is significantly different between the bacterial agent groups 1, 2, 3 and the metformin treatment group (*P value<0.05). From the perspective of overall glucose tolerance process, it can be seen that *Megamonas funiformis* can effectively ameliorate glucose intolerance in diabetic mice. Throughout the process of regulating glucose, the bacterial agent groups 1, 2, 3 showed a lower blood glucose level than the metformin treatment group at each time point, indicating that *Megamonas funiformis* has a better efficacy on ameliorating glucose intolerance in diabetic mice than metformin.

Example 5 Efficacy of *Megamonas funiformis* in a Hyperlipidemia Animal Model

Sixty C57bL/6 mice (purchased from Guangdong Medical Experimental Animal Center) at 6 weeks old were used in this experiment, which were normally fed in a Specific pathogen Free (SPF) environment. The mice were adaptively fed for 1 week and then randomly divided into 6 groups, with 10 mice in each group. The animal model is constructed along with intervention.

Model control group: the mice were fed with high-fat feed and 2 ml of phosphate buffered saline (PBS) daily;

Bacterial agent group 1: the mice were fed with high-fat feed and 2 ml of DSM 19343 bacterial solution ($1 \times 10^9$ cfu/ml) daily;

Bacterial agent group 2: the mice were fed with high-fat feed and 2 ml of AF24-28AC bacterial solution ($1 \times 10^9$ cfu/ml) daily;

Bacterial agent group 3: the mice were fed with high-fat feed and 2 ml of JCM 14723 bacterial solution ($1 \times 10^9$ cfu/ml) daily;

Tongmai Jiangzhi tablet group (a positive drug for the treatment of hyperlipidemia): the mice were fed with high-fat feed and 0.6 g/kg Tongmai Jiangzhi tablets;

Normal control group: the mice were fed with ordinary feed.

Experimental data such as the body condition, food intake amount and the like of mice was recorded every week before and after the intervention of the model. After the completion of experiment, the mice were sacrificed, and the fat content was recorded, the serum was collected for detection of blood lipid contents (including total cholesterol (TC), triglyceride (TG), high-density lipoprotein (HDLC) and low-density lipoprotein (LDLC)) in the serum according to the instruction of kit. Blood from the last carotid artery was taken for hemorheological examination.

TABLE 9

Experimental results of effect of *Megamonas funiformis* on blood lipids in mice

| Groups | TC (total cholesterol) (mmol/L) | TG (triglyceride) (mmol/L) | LDLC (low-density lipoprotein) (mmol/L) | HDLC (high-density lipoprotein) mmol/L) | blood viscosity |
|---|---|---|---|---|---|
| Model control group | 4.643 | 1.244 | 2.658 | 3.312 | 2.34 |
| Tongmai Jiangzhi tablet group | 4.022 | 0.948 | 1.642 | 3.213 | 1.32 |
| Bacterial agent group 1 | 4.013* | 0.922* | 1.494* | 3.321 | 1.28* |
| Bacterial agent group 2 | 4.011* | 0.913* | 1.485* | 3.309 | 1.31* |
| Bacterial agent group 3 | 4.015* | 0.932* | 1.523* | 3.211 | 1.25* |
| Normal control group | 3.534 | 0.835 | 1.456 | 3.257 | 1.02 |

The main components of blood lipid are cholesterol and triglyceride, in which the increase of cholesterol and triglyceride levels in plasma is closely related to the onset of atherosclerosis.

It can be seen from Table 9 that the intervention of *Megamonas funiformis* can effectively control the levels of TC, TG, LDLC in blood and blood viscosity relative to the model control group (*P<0.05), achieving a similar efficacy to that of Tongmai Jiangzhi tablet, indicating that *Megamonas funiformis* can indeed reduce blood lipids and indicators related to atherosclerosis-related disease (such as cardiovascular disease) as well as significantly reduce blood viscosity, thereby effectively preventing the blood from being a state of high viscosity and high coagulation, thus ameliorating hemorheology and vascular disease.

Example 6 Efficacy of *Megamonas funiformis* on Experimental Myocardial Ischemia in Rats Fifty SD rats (purchased from Guangdong Medical Experimental Animal Center, half male and half female) at 180-220 g of body weight and 6 weeks old were used in this experiment, which were normally fed in a Specific pathogen Free (SPF) environment. The rats were adaptively fed for 1 week and then randomly divided into 5 groups, with 10 rats in each group.

Model group: the rats were fed with 2.5 ml/kg PBS by gavage daily for 10 consecutive days;

Bacterial agent group 1: the rats were fed with 2.5 ml/kg DSM 19343 bacterial solution ($1\times10^9$ cfu/ml) by gavage daily for 10 consecutive days;

Bacterial agent group 2: the rats were fed with 2.5 ml/kg AF24-28AC bacterial solution ($1\times10^9$ cfu/ml) by gavage daily for 10 consecutive days;

Bacterial agent group 3: the rats were fed with 2.5 ml/kg JCM 14723 bacterial solution ($1\times10^9$ cfu/ml) by gavage daily for 10 consecutive days;

FuFangDanShen tablet group: the rats were fed with 2 g/kg FuFangDanShen tablet (SFDA approval number Z21020381, Tianjin Tasly (Liaoning) Pharmaceutical Co., Ltd.) by gavage daily for 10 consecutive days.

For each group, the standard lead I electrocardiogram was recorded post 1 hour of last administration, followed by sublingual intravenous injection (iv.) with pituitrin (SFDA approval number H31022259, specifications: 2 ml: 6 units, from Shanghai First Biochemical & Pharmaceutical Industry Co., Ltd.) in 1 unit/kg (in a volume of 1 ml/kg) within 15 seconds, after which the change of electrocardiogram was recorded post 5 seconds, 15 seconds, 30 seconds, 1 minute, 2 minutes, 3 minutes and 5 minutes, and the change of ST segment displacement before and after administration of pituitrin was measured and compared, with statistical analysis by using t test between groups. The specific experimental results are shown in Table 10.

TABLE 10

Effect of bacterial agent and Danshen tablet on ST-segment displacement of rat myocardial ischemia induced by pituitrin

| Groups | ST-segment displacement (mv) (±S) |
|---|---|
| Model group | 0.058 ± 0.012 |
| FuFangDanShen tablet group | 0.034 ± 0.014* |
| Bacterial agent group 1 | 0.019 ± 0.011** |
| Bacterial agent group 2 | 0.018 ± 0.012** |
| Bacterial agent group 3 | 0.020 ± 0.012** |

According to the statistics in Table, the *Megamonas funiformis* provided in the present disclosure can effectively reduce the ST segment displacement of myocardial ischemia in rats relative to the model group (**P<0.01, *P<0.05), indicating that the bacterial agents provided in the present disclosure have an excellent relieving and protective effect on myocardial ischemia, and the effect of which is superior than that of the FuFangDanShen tablet group.

Example 7 Efficacy of *Megamonas funiformis* in a Hyperuricemia Animal Model

The hyperuricemia animal model is constructed by using C57bL/6 mice (purchased from Guangdong Medical Experimental Animal Center) at 8 weeks old and 20±2 g of body weight. The mice are housed in a specific pathogen free (SPF) environment and adaptively fed for 1 week, followed by grouping and modeling. The hyperuricemia animal model is induced by feeding with a feed containing 5% oteracil potassium, and the mice having fasting blood uric acid value reaching 0.42 mM/L or above can be used as a hyperuricemia mice model. Fifty mice selected for experiments are randomly divided into 5 groups.

Model group: the hyperuricemia mice model was administered with saline solution by gavage;

Bacterial agent group 1: the hyperuricemia mice model was treated with the DSM 19343 bacterial solution ($1\times10^8$ cfu/ml) by gavage;

Bacterial agent group 2: the hyperuricemia mice model was treated with the AF24-28AC bacterial solution ($1\times10^8$ cfu/ml) by gavage;

Bacterial agent group 3: the hyperuricemia mice model was treated with the JCM 14723 bacterial solution ($1\times10^8$ cfu/ml) by gavage;

Indomethacin treatment group: the hyperuricemia mice model was treated with the positive drug indomethacin.

The experiment was carried out based on the different groups. After the construction of hyperuricemia mice model (i.e., FBG>10), the treatment was started and lasted for 2 months. The food intake amount of mice was recorded daily. Blood of mice was collected from the tail vein every week for detection of fasting blood uric acid value.

TABLE 11

Experimental results of effect of *Megamonas funiformis* AF24-28AC on fasting blood uric acid in mice model

| Groups | Week 1 (mmol/L) | Week 3 (mmol/L) | Week 5 (mmol/L) | Week 7 (mmol/L) | Week 9 (mmol/L) |
|---|---|---|---|---|---|
| Model group | 7.5 | 8.1 | 7.9 | 7.2 | 7.3 |
| Bacterial agent group 1 | 6.8 | 5.9 | 4.6 | 2.5 | 0.9* |
| Bacterial agent group 2 | 6.8 | 5.5 | 3.6 | 1.5 | 0.9* |
| Bacterial agent group 3 | 7.0 | 6.0 | 4.2 | 1.9 | 1.0* |
| Indomethacin treatment group | 6.9 | 6.3 | 4.5 | 2.8 | 1.7* |

The results in Table 11 show that the fasting blood uric acid value of mice in the bacterial agent groups 1, 2 and 3 as well as the indomethacin treatment group gradually decreases as the treatment progresses, thus the blood uric acid value of the mice tends to be normal, with significant effect of decreasing uric acid value. This indicates that the *Megamonas funiformis* can effectively reduce blood uric acid compared to the model group (*P value<0.05). Meanwhile, the blood uric acid value of mice in the *Megamonas funiformis* bacterial agent groups is lower than that of mice in the indomethacin treatment group, indicating that *Megamonas funiformis* has a better efficacy on decreasing fasting blood uric acid than indomethacin.

Example 8 Food Composition Containing *Megamonas funiformis* AF24-28AC

Raw materials and proportion thereof were shown in Table 12.

TABLE 12

| Raw material(s) | Mass percentage (%) |
|---|---|
| *Megamonas funiformis* AF24-28AC | 0.5 |
| milk | 90.0 |
| sugar | 9.0 |
| Vitamin C | 0.5 |

Milk and sugar in proportion of formula as above were mixed, stirred to complete mixture, preheated, homogenized at the pressure of 20 Mpa, and then sterilized at about 90° C. for 5 to 10 mins, cooled to 40 to 43° C., followed by adding a protective agent (Vitamin C) and inoculation of $1\text{-}100\times10^6$ cfu/g *Megamonas funiformis* AF24-28AC, thus obtaining the food composition containing *Megamonas funiformis* AF24-28AC.

Example 9 Pharmaceutical Composition Containing *Megamonas funiformis* AF24-28AC Raw materials and proportion thereof were shown in Table 13.

TABLE 13

| Raw material(s) | Mass percentage (%) |
|---|---|
| *Megamonas funiformis* AF24-28AC | 1.0% |
| lactose | 2.0% |
| yeast powder | 2.0% |
| peptone | 1.0% |
| purified water | 93.5% |
| vitamin C | 0.5% |

Lactose, yeast powder and peptone in proportion were mixed with purified water to be uniform, preheated to 60 to 65° C., homogenized at the pressure of 20 Mpa, and then sterilized at about 90° C. for 20 to 30 mins, cooled to 36 to 38° C., followed by adding vitamin C and inoculation of 1-50×10$^6$ cfu/mL active *Megamonas funiformis* AF24-28AC, after which fermented at 36 to 38° C. to pH 6.0, centrifuged, freeze-dried to less than 3% of water content, thus obtaining a freeze-dried product containing *Megamonas funiformis* AF24-28AC. 0.5 g of the freeze-dried product containing *Megamonas funiformis* AF24-28AC was weighed, mixed with an equal amount of maltodextrin and a protective agent (such as vitamin C, cysteine), and then encapsulated into capsules, thus obtaining the pharmaceutical composition containing *Megamonas funiformis* AF24-28AC.

Example 10 Method of Preparing a Medicine for the Treatment of Metabolic Diseases 1. Preparation of Bacterial Solution

*Megamonas funiformis* AF24-28AC (1×10$^9$ cfu/ml) were anaerobically fermented in the PYG medium at 37° C. for 2 to 3 days.

2. Preparation of Growth Factors

The skimmed milk and casein were mixed, centrifuged and ultra-filtered to obtain a crude extract of milk growth factor, including nutrients of vitamins, purines and/or pyrimidines.

3. Manufacture of a Medicament or Pharmaceutical Dosage Form 5 volumes (ml) of growth factor and 1 volume (ml) of protective agent (such as vitamin C, cysteine) were added to 100 volumes (ml) of the fermented bacterial solution of *Megamonas funiformis* AF24-28AC, fully stirred to be uniform, and then added with starch excipients (such as maltodextrin), thus obtaining the medicament or pharmaceutical dosage form containing *Megamonas funiformis* AF24-28AC.

The present disclosure is illustrated by specific examples as above, and these examples are only for understanding the present disclosure and do not limit the scope of the present disclosure. Several simple deductions, modifications or substitutions can be made by those skilled in the art according to the concept of the present disclosure.

What is claimed is:

1. A method for treating metabolic diseases, comprising:
administering a *Megamonas funiformis* or a composition comprising the *Megamonas funiformis* to a subject in need to treat the metabolic disease,
wherein the *Megamonas funiformis* is *Megamonas funiformis* AF24-28AC with a deposit number of GDMCC 60093 or *Megamonas funiformis* JCM 14723, or a combination thereof,
wherein the metabolic disease is selected from the group consisting of myocardial ischemia, hyperuricemia or a combination thereof.

2. The method according to claim 1, wherein the *Megamonas funiformis* or the composition is administered orally.

3. The method according to claim 1, wherein the subject comprises human or non-human mammal.

4. The method according to claim 1, wherein the composition comprises: (a) an effective amount of *Megamonas funiformis* and/or its metabolites, and (b) a food acceptable or pharmaceutically acceptable carrier.

5. The method according to claim 1, wherein the composition comprises $1\times10^{-1}$ to $1\times10^{20}$ cfu/mL or $1\times10^{-1}$ to $1\times10^{20}$ cfu/g of *Megamonas funiformis*, based on the total volume or total weight of the composition.

6. The method according to claim 1, wherein the composition further comprises one or both of probiotics and prebiotics.

7. The method according to claim 1, wherein the composition further comprises a substance capable of maintaining the vitality of *Megamonas funiformis*.

8. The method according to claim 1, wherein the composition is selected from the group consisting of a food composition, a health care composition, a pharmaceutical composition, a beverage composition, a feed composition, or a combination thereof.

9. The method according to claim 1, wherein the *Megamonas funiformis* exhibits one or more activities from the group consisting of:

(i) reducing a blood glucose level in mammals;
(ii) ameliorating glucose intolerance in mammals;
(iii) ameliorating myocardial ischemia in mammals;
(iv) reducing a blood uric acid level in mammals;
(v) reducing a blood lipid level in mammals;
(vi) reducing body weight of mammals; and
(vii) ameliorating vasculopathy in mammals.

10. The method according to claim 1, wherein the composition is in a unit dosage form.

11. The method according to claim 6, wherein the probiotics are selected from the group consisting of Lactic acid bacteria, Bifidobacteria, *Lactobacillus acidophilus* or a combination thereof,
the prebiotics are selected from the group consisting of fructooligosaccharide (FOS), galactooligosaccharide (GOS), xylooligosaccharide (XOS), lactosucrose (LACT), soybean oligosaccharides (SOS), Inulin, oligosaccharide or a combination thereof.

12. The method according to claim 1, wherein an administration dosage is 0.01 to 5 g/50 kg body weight per day.

13. The method according to claim 1, wherein the composition comprises $1\times10^4$ to $1\times10^{15}$ cfu/mL or $1\times10^4$ to $1\times10^{15}$ cfu/g of *Megamonas funiformis*, based on the total volume or total weight of the composition.

14. The method according to claim 10, wherein the unit dosage form is one tablet, one capsule or one vial.

15. The method according to claim 10, wherein the composition in each unit dosage form is of a mass of 0.05 g to 5 g.

16. The method according to claim 10, wherein the composition in each unit dosage form is of a mass of 0.1 g to 1 g.

17. The method according to claim 1, wherein an administration dosage is 0.1 to 2 g/50 kg body weight per day.

18. A method for retarding metabolic diseases, comprising:
administering a *Megamonas funiformis* or a composition comprising the *Megamonas funiformis* to a subject in need to treat the metabolic disease, wherein the *Megamonas funiformis* is *Megamonas funiformis* AF24-28AC with a deposit number of GDMCC 60093 or *Megamonas funiformis* JCM 14723, or a combination thereof, wherein the metabolic disease is selected from the group consisting of myocardial ischemia, hyperuricemia or a combination thereof.

19. A method for treating metabolic diseases, comprising:

administering a *Megamonas funiformis* or a composition comprising the *Megamonas funiformis* to a subject in need to treat the metabolic disease, wherein the *Megamonas funiformis* is *Megamonas funiformis* AF24-28AC with a deposit number of GDMCC 60093 or *Megamonas funiformis* JCM 14723, or a combination thereof, wherein the metabolic disease is selected from the group consisting of obesity, diabetes, hyperlipidemia, myocardial ischemia, hyperuricemia or a combination thereof, wherein the composition is in a unit dosage form, wherein the composition in each unit dosage form is of a mass of 0.05 g to 5 g.

\* \* \* \* \*